United States Patent [19]

Ichihara

[11] Patent Number: 4,904,870
[45] Date of Patent: Feb. 27, 1990

[54] DEVICE AND METHOD FOR CORRECTING SENSITIVITY OF A GAMMA CAMERA

[75] Inventor: Takashi Ichihara, Tokyo, Japan

[73] Assignee: Kabushiki Kaisha Toshiba, Kawasaki, Japan

[21] Appl. No.: 245,280

[22] Filed: Sep. 16, 1988

[30] Foreign Application Priority Data

Sep. 18, 1987 [JP] Japan .................. 62-234416

[51] Int. Cl.$^4$ .................. G01T 1/20; G01T 1/164
[52] U.S. Cl. .................. 250/363.07; 250/363.01; 364/571.01
[58] Field of Search .......... 364/525, 526, 570, 571.01; 250/363.01, 363.07

[56] References Cited

U.S. PATENT DOCUMENTS

| | | | |
|---|---|---|---|
| 4,060,726 | 11/1977 | Luitwieler et al. | 250/363.01 X |
| 4,424,446 | 1/1984 | Inbar et al. | 250/363.07 |
| 4,429,226 | 1/1984 | Inbar | 250/363.07 |
| 4,582,995 | 4/1986 | Lim et al. | 250/363.07 |
| 4,588,897 | 5/1986 | Inbar et al. | 250/363.07 |
| 4,695,964 | 9/1987 | Seto et al. | 364/571.01 X |

Primary Examiner—Constantine Hannaher
Assistant Examiner—J. Eisenber
Attorney, Agent, or Firm—Oblon, Spivak, McClelland, Maier & Neustadt

[57] ABSTRACT

A gamma camera sensitivity correction device and method which utilizes the fact that the collimator's characteristic correction coefficients do not change with time, wherein first of all the collimator's characteristic sensitivity data are found, and then freshly collected detector characteristic uniformity data are found with the collimator removed. From the collimator's characteristic sensitivity data and detector's characteristic uniformity data, uniformity data in the condition that the collimator is mounted on the detector are derived. Then, correction coefficients are determined based on these derived uniformity data. In this way, the uniformity correction matrix for sensitivity correction can be found with a small radiation source in a short time.

12 Claims, 5 Drawing Sheets

DEVICE AND METHOD FOR CORRECTING SENSITIVITY OF A GAMMA CAMERA

BACKGROUND OF THE INVENTION

1. Field of the Invention

This invention relates to a gamma camera sensitivity correcting device and method that corrects the sensitivity of a gamma camera.

2. Discussion of Background

When a gamma camera is used, a subject is dosed with a radio-isotope (hereinbelow abbreviated to RI), the amount of this RI that is selectively accumulated in a specific organ or disease site is detected, and imaged as an accumulation image.

The main parts of a gamma camera are shown in FIG. 1. Reference numeral designates a detector that detects radiation (gamma rays) from the RI. It consists of a scintillator 17, light guide 18, photoelectron multiplier tubes 19, and pre-amplifiers 20. Gamma rays cannot be refracted and focussed by a lens as in an optical camera, so that a collimator 16 is arranged ahead of detector 15. Collimator 16 is built around a lead sheet provided with a large number of parallel holes. By this means an image of the same size as the subject is created at the surface of scintillator 17.

In scintillator 17, photoelectron multiplier tubes (PMTs) 19 are arranged in a hexagonally close-packed fashion on the other side of light-guide 18, which is constructed of a transparent substance (lucite or the like). A large number (19, 37 or 61) of PMTs 19, of 2-inch or 3-inch diameter, are used, arranged in a hexagonal pattern. When gamma rays are incident on scintillator 17, their energy is absorbed, causing fluorescence at the point of absorption. This light is input via light guide 18 to PMTs 19, where it is subjected to a photoelectric conversion, so that output pulses proportional to the incoming light are output from each PMT 19. If light is emitted directly below a given PMT, the largest output will be obtained from that PMT; or, alternatively, if light is emitted at a point between three PMTs, equal output will obtained from those three PMTs. Thus the point of luminescence, i.e., the position of gamma ray incidence, can be found from the output pulses of PMTs 19. Using the values of X and Y of an orthogonal coordinate system whose origin is at the center of scintillator 17, adder 21 multiplies the outputs of the respective PMTs 19 by coefficients (called "weights") that depend on the positional coordinates of the respective PMT and adds them, to obtain signals for the various directions $X+$, $X-$, $Y+$, and $Y-$.

In addition to this, if the outputs of all the PMTs 19 are multiplied by a constant coefficient and then added, the resultant signal will be proportional to the total luminescence of the scintillator, i.e., to the energy of the gamma ray. This is therefore termed the energy signal or Z signal. This Z signal is amplified by amplifier 22, then input to pulse wave height analyzer 25, so that only gamma rays of the required preset energy are selected. The $X+$, $X-$, $Y+$, and $Y-$ position signals and the Z signal are each amplified and then the signals of the selected gamma rays only are input to a waveform expanding circuit 23, from the output of which signals:

$$X = \frac{X+ \; - \; X-}{Z}, \; Y = \frac{Y+ \; - \; Y-}{Z}$$

are obtained. The reason for dividing by Z is to make the magnitude of the image independent of the gamma ray. These X and Y signals are applied to the deflecting input of a cathode ray oscilloscope (CRT). The output of pulse wave height analyzer 25 is applied to a spot generating circuit 26, so that each incoming gamma ray is displayed as a luminous point on CRT 27. A 2-dimensional image can be obtained by recording and accumulating these luminous points on polaroid film or X-ray film by means of a lens. It is also possible to record and accumulate the frequency with which gamma rays arrive in an IC memory corresponding to X and Y and to obtain a functional diagnostic image by carrying out data processing on the data stored in this IC. FIG. 2 shows a case where such a functional diagnostic image is obtained.

Position signals X and Y are input through A/D converters 2 and 3 to correction table 5 and linear correction part 6. From correction table 5, correction values $a_i(X,Y)$, $b_i(X,Y)$, $c_i(X,Y)$, and $d_i(X,Y)$; (where $i = 1, 2, \ldots$) corresponding to the X and Y signals are output, and these are then input to linear correction part 6. This linear correction part 6 finds X' and Y' by calculating $$X' = a_1 X + b_1 Y + c_1 XY + d_1$$

$$Y' = a_2 X + b_2 Y + c_2 XY + d_2$$

The Z signal is also input to correction part 7, where it is corrected by performing the calculation $$Z' = e(X,Y) \cdot Z$$

This corrected data Z' is input to window circuit 9, constituting the next stage, and, if this input Z' is of a prescribed energy value, it causes the pixel value of the corresponding address of image data memory 10 to be incremented by $+1$. The memory content of image data memory 10 is input to main CPU (central processing unit) 8 through line 11 and the values of Z, X, and Y are input to main CPU 8 through lines 12 and 13, where calculation and rewriting of the correction coefficients are performed. Main CPU 8 performs a sensitivity correction on the contents of image data memory 10 in accordance with correction coefficients f(i,j). In collection modes such as single photon emission CT (hereinbelow termed "ECT") where strict uniformity etc. is required, main CPU 8 performs sensitivity correction in accordance with:

$$N'(i,j) = f(i,j) \times N(i,j)$$

where (i,j) are the memory addresses corresponding to (X,Y).

Since there is a timewise variation of the output wave height of photoelectron multiplier tube 19 due to optical coupling of scintillator 17 and light guide 18, or to variation of the characteristic of photoelectron multiplier 19 etc., it is necessary to re-write the correction data of Z correcting part 7 periodically, to match these changed circumstances.

Furthermore, being made of a metal, such as lead, of high gamma ray screening ability, collimator 16 shows differences in the proportion of gamma rays that it lets through, depending on the precision with which it was machined and on the location (X,Y). Consequently, in the case of ECT, there were the problems that ring-shaped artifacts were formed in the reconstructed image due to statistical scatter in the uniformity of the sensitivity of the gamma camera, or that artifacts were produced with lapse of time (however, such artifacts are not produced if the correction data are re-written to match time-wise variation, as mentioned above). This correction of uniformity of sensitivity for the ECT collection purposes was carried out by creating a correction table (matrix) from the uniformity data of detector 15 (scintillator+light guide+photoelectron multiplier)+electrical system+collimator 16, and implementing a sensitivity correction as (collimator+detector) by multiplying the data in image data memory 10 by these coefficients. In this case, a change in the sensitivity of the whole system is seen due to the time-wise variation of the sensitivity of detector 15. Conventionally, to obtain correction data, the following steps (1) to (3) are necessary:

(1) find the correction coefficient of the Z correction part 7 by removing the collimator;

(2) find the correction coefficient of linear interpolation part 6 by mounting a phantom for X-Y correction (linear correction) on the detector;

(3) find the uniformity correction matrix by collecting uniformity data with (collimator+detector) using a uniform linear source, by mounting collimator 16 on detector 15 after (1) and (2) above.

However, the data collection required for sensitivity correction of the detector with collimator fitted (step (3) above) usually takes 2 to 3 hours, and it is difficult to perform this data collection frequently, since there are a number of different types of collimators.

SUMMARY OF THE INVENTION

Accordingly, the object of this invention is to provide a gamma camera sensitivity correction device and method whereby the uniformity correction matrix for sensitivity correction can be obtained rapidly.

The above and other objects are achieved by providing a gamma camera sensitivity correction device whereby radiation from a radioisotope administered to a subject is detected and used to obtain a radioisotope accumulation image of said subject, including first calculating means for determining sensitivity data that are characteristic of the collimator; means for freshly collecting uniformity data that are characteristic of the detector itself in the condition where the collimator is removed; means for deriving uniformity data in the condition where the collimator is mounted on the detector, based on the uniformity data from this collection means, that are characteristic of the detector itself, and on the sensitivity data from said first calculating means, that are characteristic of the collimator; and second calculating means for determining the uniformity correction coefficients for correcting the radioisotope accumulation image, based on the uniformity data from this derivation means.

Since the correction coefficients that are characteristic of the collimator do not vary with time, this sensitivity data that is characteristic of the collimator is stored beforehand in the memory means. The correction coefficients to be finally applied are found from the uniformity data that are derived in the condition in which the collimator is mounted on the detector, based on uniformity data that are characteristic of the detector (these being freshly collected with the collimator removed) and on the aforementioned sensitivity data that is characteristic of the collimator. Thus, in the compilation of the final uniformity correction matrix, the uniformity data that are characteristic of the detector can be collected with the collimator removed, which makes it possible to do this in a short time, using a small radiation source.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 3:
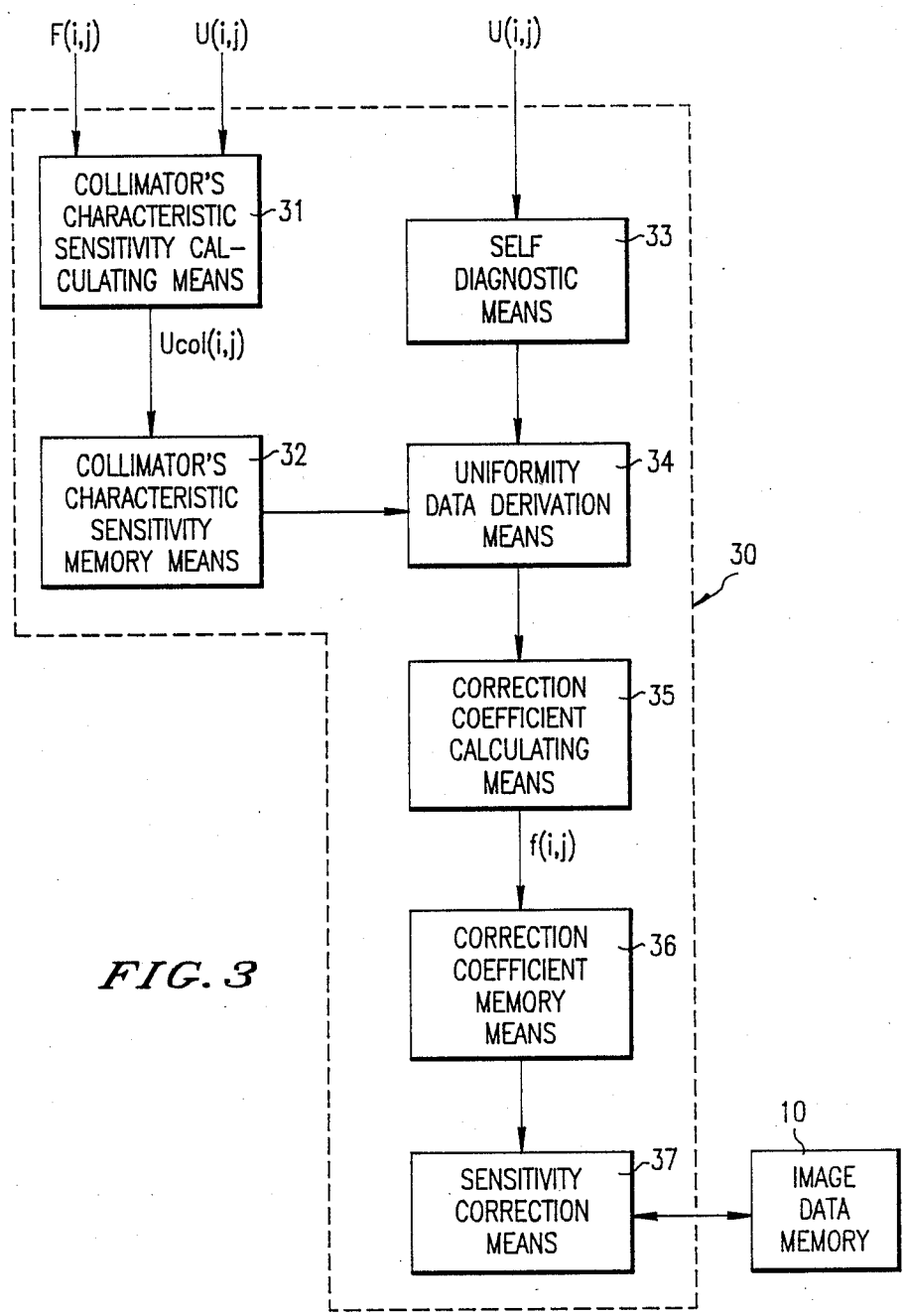
FIG. 3 is a block diagram of the layout of a gamma camera sensitivity correction device according to an embodiment of the present invention.

Referring now to the drawings, wherein like reference numerals designate identical or corresponding parts throughout the several views, and more particularly to FIG. 3 thereof, there is shown an embodiment of a gamma camera sensitivity correction device according to the present invention.

As shown in FIG. 3, the device 30 of this embodiment is provided with: collimator characteristic sensitivity calculating means 31, collimator characteristic sensitivity memory means 32, self diagnostic means 33, uniformity data derivation means 34, correction coefficient calculating means 35, correction coefficient memory means 36, and sensitivity correction means 37.

Figure 1:
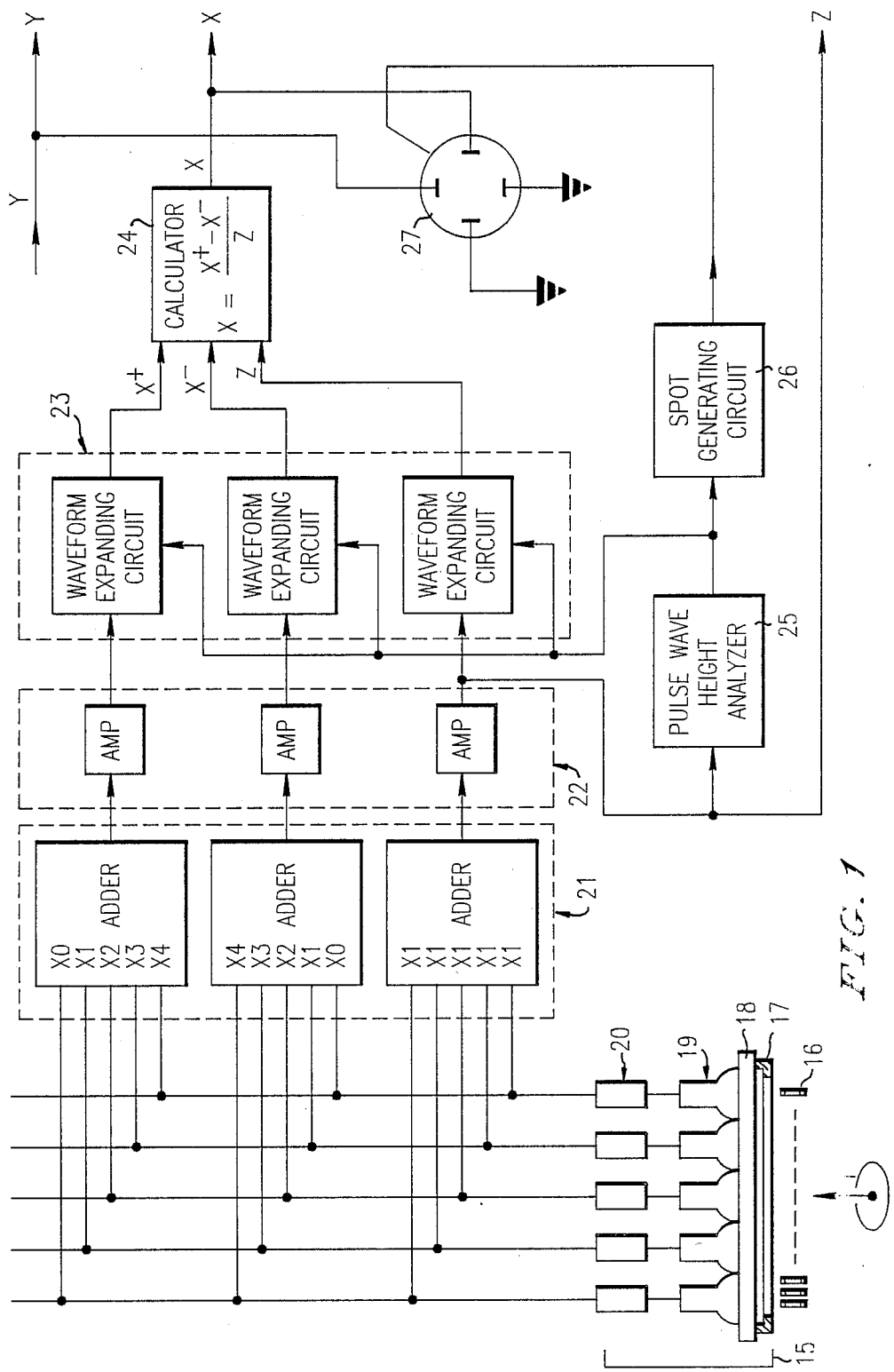
FIG. 1 is a block diagram showing the main parts of a conventional gamma camera.

The collimator characteristic sensitivity calculating means 31 finds the sensitivity data Ucol(i,j) that are characteristic of the collimator from uniformity data F(i,j) that are collected in the condition with collimator 16 (see FIG. 1) mounted on detector 15 and from uniformity data U(i,j) that are collected with collimator 16 removed, by performing the calculation of the following equation (1):

$$Ucol(i,j) = F(i,j)/U(i,j) \quad (1)$$

The data Ucol(i,j) that are found by the collimator characteristic sensitivity calculating means 31 are written to collimator characteristic sensitivity memory means 32, which is located in a subsequent stage. Thus a table of the collimator's characteristic sensitivity is formed in the memory means 32.

To compile the uniformity correction matrix of the detector with the collimator 16 mounted, self diagnostic means 33 finds the difference between the data U(i,j) freshly collected with the collimator removed and the previously collected U(i,j) data. Depending on the magnitude of the difference between these two, it discriminates whether compilation of a uniformity correction matrix is appropriate or not. If it decides that it is appropriate, it sends the U(i,j) data to uniformity data derivation means 34.

This uniformity data derivation means 34 derives the uniformity data in the condition where detector 15 is fitted with collimator 16 (i.e., "detector with collimator mounted"), based on the freshly collected data U(i,j) and data Ucol(i,j) in collimator's characteristic sensitivity memory means 32. If this uniformity data i represented as F'(i,j), this F'(i,j) is derived by performing the calculation of equation (2) below.

$$F'(i,j) = U(i,j) \cdot Ucol(i,j) \qquad (2)$$

This data F'(i,j) derived by uniformity data derivation means 34 is then sent to correction coefficient calculating means 35 that is provided in the next processing stage.

Based on these input derived data F'(i,j), this correction coefficient calculating means 35 finds the uniformity correction coefficients, represented as f(i,j), for correcting the RI accumulated image. These uniformity correction coefficients f(i,j) are derived by performing the calculation f the following equation (3):

$$f(i,j) = \frac{F(i,j)}{\sum_{i=0, j=0}^{x,y} F(i,j)/x \cdot y} \qquad (3)$$

where x.y means the total number of pixels in one RI accumulation image frame. The thus found correction coefficients f(x,y) are stored in correction coefficient memory means 36 provided in the next subsequent stage, so that a correction table is formed in this correction coefficient memory means 36. This table constitutes the uniformity correction matrix of the detector with collimator mounted.

Figure 2:
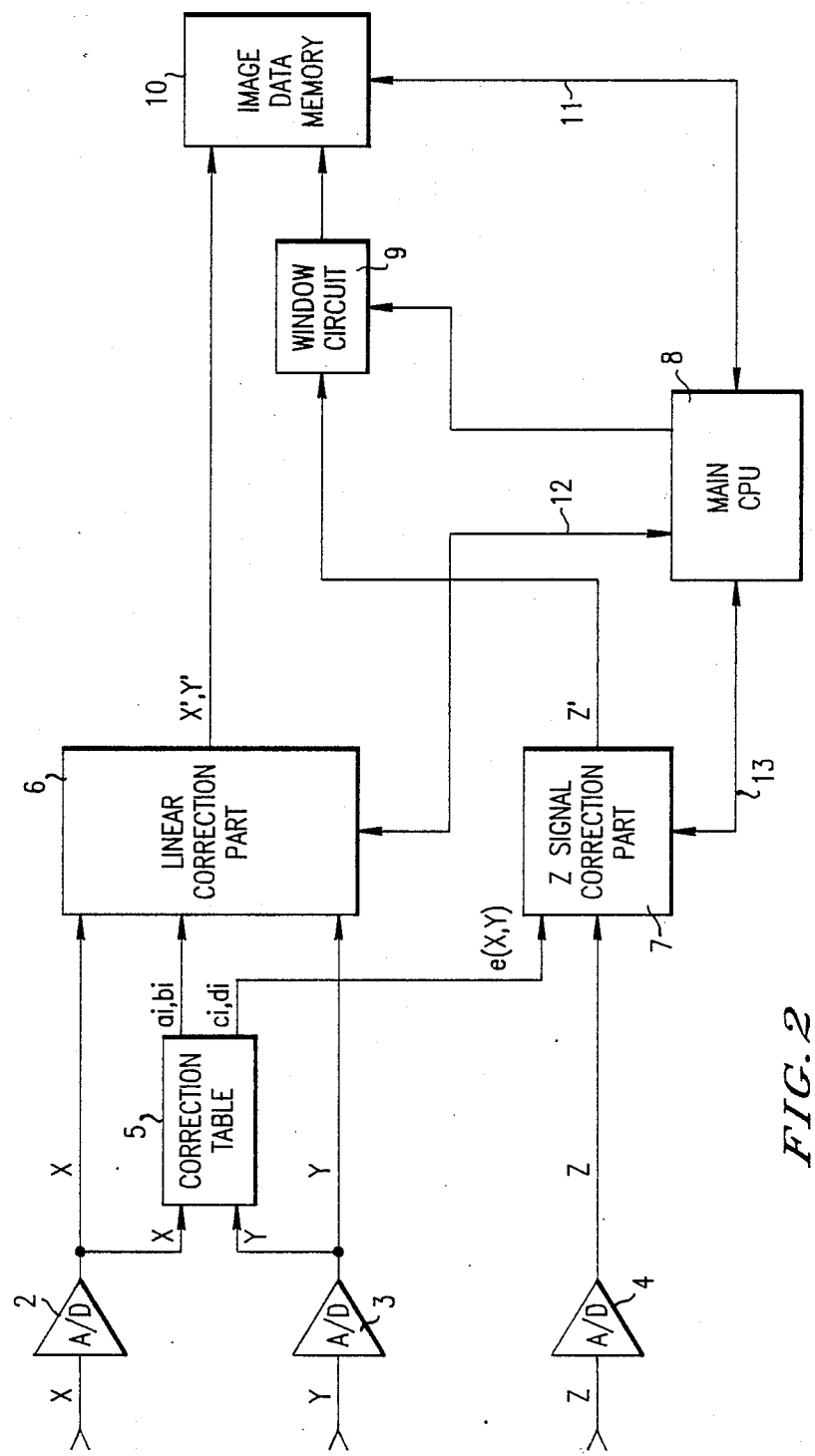
FIG. 2 is a block diagram showing the main parts of a gamma camera used to obtain a functional diagnostic image.

Sensitivity correction means 37 performs sensitivity correction as (collimator+detector) using this uniformity correction matrix. This sensitivity correction is performed by multiplying the image data, i.e., the RI accumulated image data, in image data memory 10 by the correction coefficients held in correction coefficient memory means 36. This image data memory 10 corresponds to that indicated by the same reference numeral in FIG. 2.

The collimator characteristic sensitivity calculating means 31, self diagnostic means 33, uniformity data derivation means 34, correction coefficient calculating means 35, and sensitivity correction means 37 are functionally implemented by a CPU (central processing device).

Figures 4, 5:
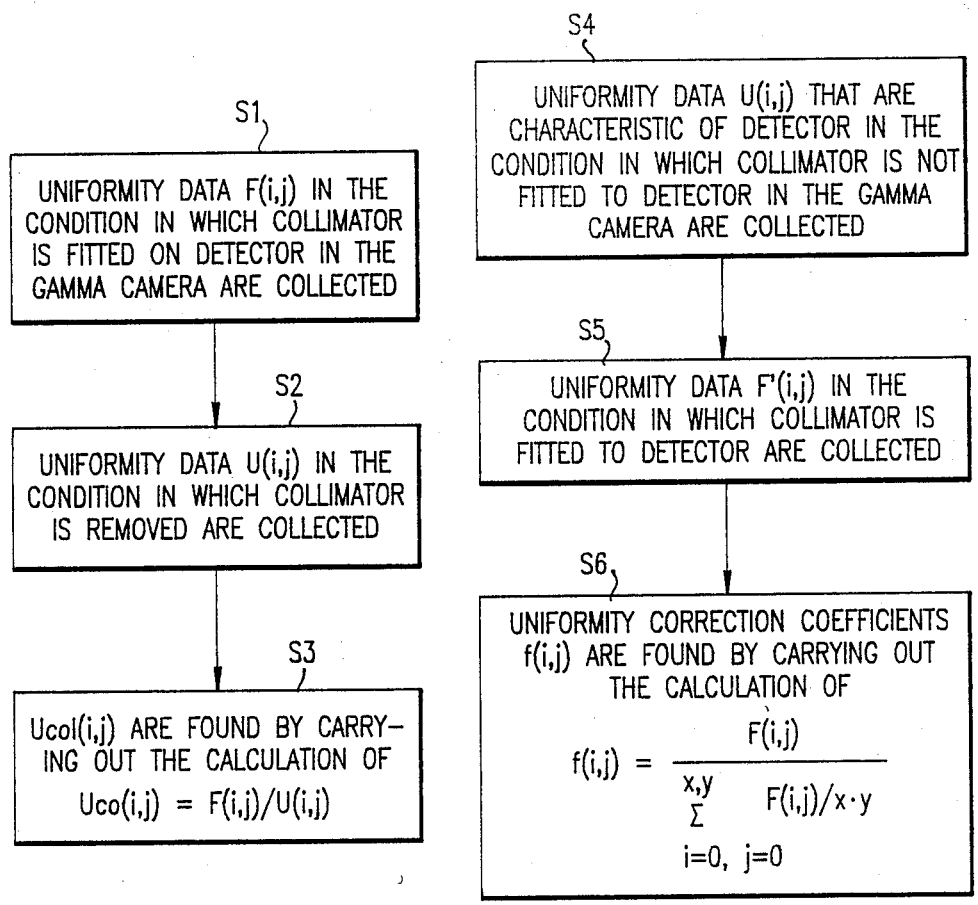
FIG. 4, FIG. 5, and FIG. 6 are flow charts provided in explanation of the operation of the device of FIG. 3.
Figure 6:
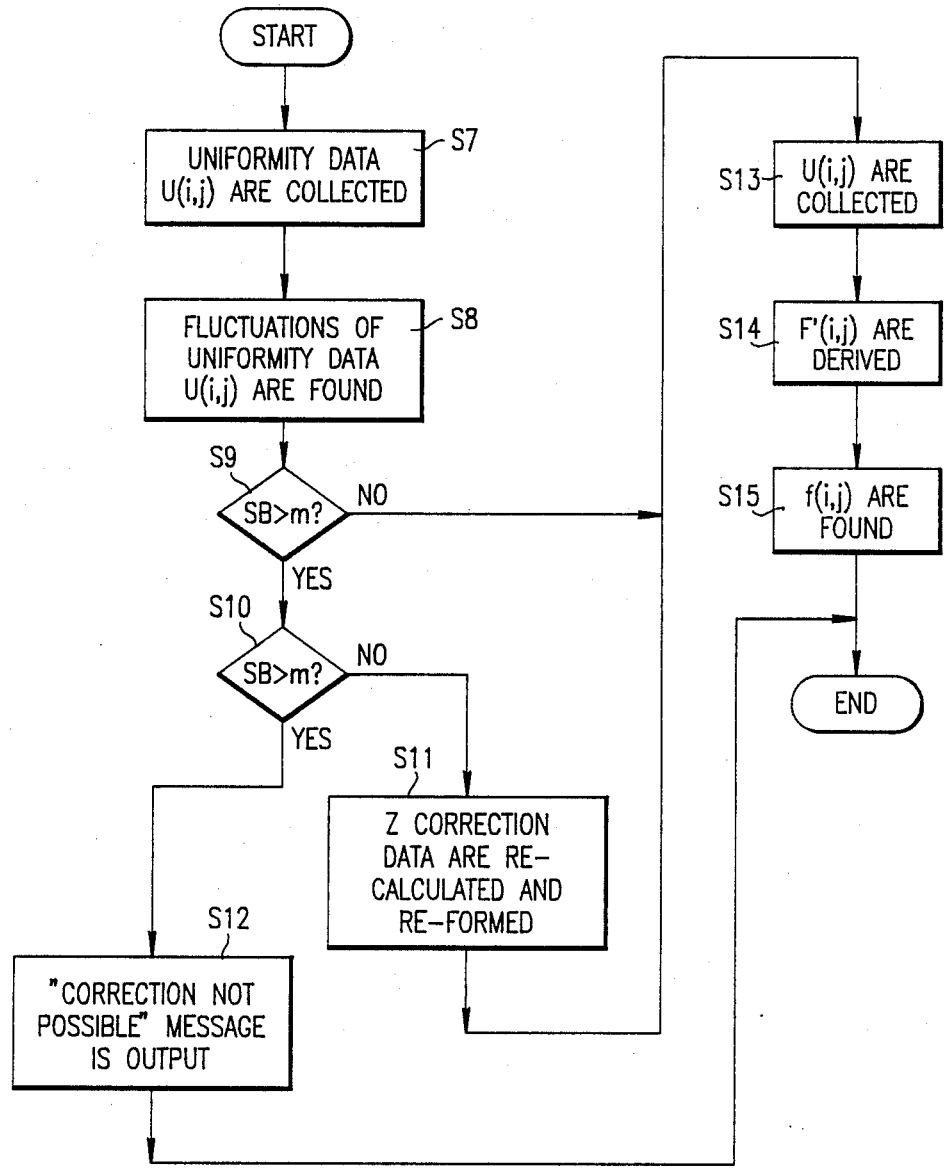

The operation of the device of the embodiment constructed as above will now be described with reference to the flow charts of FIG. 4 through FIG. 6.

In compiling the uniformity correction matrix (correction table in correction coefficient memory means 36) in the device of this embodiment, the sensitivity correction table that is characteristic of collimator 16 is already formed in the collimator characteristic sensitivity memory means 32. This sensitivity correction table is found by collimator's characteristic sensitivity calculating means 31. Specifically, as shown in FIG. 4, the uniformity data F(i,j) in the condition in which collimator 16 is fitted on detector 15 in the gamma camera are collected (sl), then, the uniformity data U(i,j) in the condition in which this collimator 16 is removed are collected (S2). Thereupon, these data F(i,j) and U(i,j) are input to the collimator characteristic sensitivity calculating means 31, where Ucol(i,j) are found by carrying out the calculation of equation (1) above. In cases where a sensitivity correction table of the Ucol(i,j) of the collimator in question has been already formed, carrying out steps S1 to S3 may be unnecessary (for example, it is planned that the manufacturer may provide a recording medium containing the sensitivity correction table Ucol(i,j), when such a collimator is shipped).

The uniformity correction matrix is compiled as follows. (For convenience in the description, steps relating to self-diagnosis are omitted).

First of all, the uniformity data U(i,j) that are characteristic of detector 15 in the condition in which collimator 16 is not fitted to detector 15 in the gamma camera are collected (S4). These data U(i,j) are input to uniformity data derivation means 34. This uniformity data derivation means 34 derives the uniformity data F'(i,j) in the condition in which collimator 16 is fitted to detector 15 (S5). This derivation is performed by carrying out the calculation of equation (2) given above. Next, when these uniformity data F'(i,j) are output to correction coefficient calculating means 35, the calculation of equation (3) given above is performed by this calculating means 35, to derive uniformity correction coefficients f(i,j) (S6). The thus-found coefficients f(i,j) are then written into correction coefficient memory means 36, thereby forming the uniformity correction matrix.

In compilation of the above uniformity correction matrix, the collimator's characteristic sensitivity data are treated as known, and only the uniformity data U(i,j) that are characteristic of the detector with collimator 16 removed are collected. Since collimator 16 is not fitted, this collection of uniformity data that are characteristic of the detector can be completed in a short time (about 10 to 20 minutes) using a small radiation source. The time required for data collection can therefore be greatly shortened as compared with the time of 2 to 3 hours that was previously necessary for the collection of data to compile the uniformity correction matrix (data collection with collimator mounted). This shortening of the data collection time means that compilation of the uniformity matrix (re-writing of the correction table of correction coefficient memory means 36) can be performed frequently. This makes it possible to carry out sensitivity correction by sensitivity correction means 37 with high accuracy. For example, compilation of the uniformity matrix of the device of this invention can be carried out before the daily clinical examination, thereby increasing the stability of the gamma camera.

Self-diagnosis by self diagnostic means 33 will now be described. A flow chart of this operation is shown in FIG. 6.

First of all, the uniformity data U(i,j) that are characteristic of detector 15 with collimator 16 not mounted are collected (S7). Next, the difference (i.e., the fluctuation) SB is found (S8) between these data U(i,j) and the most recent previously collected data U(i,j). A decision is then made (S9) as to whether or not this difference SB is larger than a preset value m that was preset to take into account statistical variation. In this decision process, if a decision NO (SB>m does not hold) is made, the U(i,j) are collected (S13), F'(i,j) are derived (S14), and f(i,j) are found (S15). These steps S13, S14, and S15 correspond to steps S4, S5, and S6 of FIG. 5. Also, in the decision process of step S9, if a decision YES (SB>m) is made, a decision is now made (S10) as to whether or not this difference SB is larger than a preset value M that was pre-set as the threshold value for correction to be performed. If, in this decision process, a decision NO (SB>m does not hold) is made, this implies that this difference is not yet large enough for correction to be performed, so the Z correction data of Z correction part 7 (see FIG. 2) are recalculated and the Z correction table re-formed (S11). Processing then shifts to execution of step S13. If, in the decision process of this step S10, a decision YES (SB>M holds) is made, in view of the possibility that this may be due to a malfunction of the gamma camera, a "correction not possible" message is output, with a request for service by a maintenance engineer (S12). Self-diagnosis of the nature of the abnormality may then be performed.

Of the above steps, steps S8 to S12 are carried out by self-diagnostic means 33.

Carrying out self-diagnosis in this way makes it possible to perform the routine inspection and self-servicing of the gamma camera in an appropriate way.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. Gamma camera sensitivity correction device capable of sensitivity correction of a gamma camera including a collimator and a light detector, wherein radiation from a radioisotope administered to a subject is detected and an image of the accumulation of the radioisotope in said subject is obtained, comprising:

first calculating means for obtaining collimator characteristic sensitivity data that are characteristic of said collimator;

means for freshly collecting uniformity data that are characteristic of the detector in the condition with said collimator removed;

means for deriving uniformity data in the condition in which the collimator is fitted on said detector, based on the freshly collected uniformity data, from said collecting means, that are characteristic of the detector, and on the collimator characteristic sensitivity data from said first calculating means; and second calculating means for determining uniformity correction coefficients for radioisotope accumulation image correction, based on the uniformity data from said derivation means.

2. Device according to claim 1, further comprising:
memory means for storing the collimator characteristic sensitivity data from said first calculating means, and wherein said derivation means derives uniformity data for the condition in which a collimator is mounted on said detector, based on the detector's characteristic uniformity data from said collection means and the stored data of the collimator's characteristic sensitivity, from said memory means.

3. Device according to claim 1, wherein said correction coefficients are expressed as f(i,j), said uniformity data as F(i,j), and the total number of pixels per frame of the radioisotope accumulation image as x.y, and the uniformity correction coefficients for radioisotope accumulation image correction are determined by the following relationship:

$$f(i,j) = \frac{F(i,j)}{\sum_{i=0,j=0}^{x,y} F(i,j)/x \cdot y}.$$

4. Device according to claim 1, further comprising:
correction coefficient memory means for storing said uniformity correction coefficients determined by said second calculating means, wherein a correction table is formed in said correction coefficient memory means.

5. Device according to claim 4, further comprising:
sensitivity correction means for performing sensitivity correction using said correction table, wherein the radioisotope accumulation image data are multiplied by the correction coefficients in said correction coefficient memory means.

6. Device according to claim 4, further comprising:
self-diagnostic means for, in the formation of said correction table, determining the difference between freshly collected data and previously collected data and uses this difference to make a decision as to whether or not said to perform a sensitivity correction.

7. A method for correcting sensitivity of a gamma camera including a collimator and a light detector, wherein radiation from a radioisotope administered to a subject is detected and an image of the accumulation of the radioisotope in said subject is obtained, comprising:

a first step of obtaining collimator characteristic sensitivity data that are characteristic of said collimator;

a second step of freshly collecting uniformity data that are characteristic of the detector in the condition with said collimator removed;

a third step of deriving uniformity data in the condition in which the collimator is fitted on said detector, based on the freshly collected uniformity data, that are characteristic of the detector, and on the collimator characteristic sensitivity data from said first steps; and a fourth step of determining uniformity correction coefficients for radioisotope accumulation image correction, based on the uniformity data from said third step.

8. Method device according to claim 7, further comprising:
storing in a memory the collimator characteristic sensitivity data obtained in said first step, and wherein said third step includes deriving uniformity data for the condition in which a collimator is mounted on said detector, based on the freshly collected characteristic uniformity data from said second step and the stored data of the collimator characteristic sensitivity.

9. Method device according to claim 7, wherein said uniformity correction coefficients are expressed as f(i,j), said uniformity data as F(i,j), and the total number of pixels per frame of the radioisotope accumulation image as x,y, and the uniformity correction coefficients for radioisotope accumulation image correction are determined by the following relationship:

$$f(i,j) = \frac{F(i,j)}{\sum_{i=0,j=0}^{x,y} F(i,j)/x \cdot y}$$

10. Method according to claim 7, further comprising:
storing said uniformity correction coefficients determined in said fourth step to form a correction table in a correction coefficient memory.

11. Method according to claim 10, further comprising:
performing sensitivity correction using said correction table, wherein the radioisotope accumulation image data are multiplied by the correction coefficients in said correction coefficient memory means.

12. Device according to claim 7, further comprising:
determining whether a sensitivity correction is necessary by determining the difference between freshly collected data and previously collected data and using this difference to make a decision as to whether or not said correction table is appropriate or a correction is required.

* * * * *